US010133244B2

(12) United States Patent
Leeson et al.

(10) Patent No.: US 10,133,244 B2
(45) Date of Patent: Nov. 20, 2018

(54) CHAIR SIDE MILL FOR FABRICATING DENTAL RESTORATIONS

(75) Inventors: David Leeson, Tustin, CA (US); Dean Dohi, Anaheim, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 378 days.

(21) Appl. No.: 13/495,620

(22) Filed: Jun. 13, 2012

(65) Prior Publication Data
US 2013/0338813 A1 Dec. 19, 2013

(51) Int. Cl.
*G05B 11/32* (2006.01)
*A61C 13/00* (2006.01)
*G05B 19/4099* (2006.01)

(52) U.S. Cl.
CPC .......... *G05B 11/32* (2013.01); *A61C 13/0004* (2013.01); *G05B 19/4099* (2013.01); *A61C 13/0006* (2013.01); *G05B 2219/45167* (2013.01); *G05B 2219/49019* (2013.01)

(58) Field of Classification Search
CPC .................................................. G05B 11/32
See application file for complete search history.

(56) References Cited

U.S. PATENT DOCUMENTS

| | | | |
|---|---|---|---|
| 4,639,653 A * | 1/1987 | Anderson ............ | G05B 19/253 318/568.1 |
| 4,866,356 A * | 9/1989 | Altendorf ............ | A61C 1/0015 388/811 |
| 5,402,607 A * | 4/1995 | Lombard ............ | B23Q 1/48 451/106 |
| 5,429,459 A * | 7/1995 | Palm ............ | B23G 1/34 408/222 |
| 5,764,518 A * | 6/1998 | Collins ............ | B25J 9/1617 700/117 |
| 6,796,012 B2 | 9/2004 | Geissler et al. | |
| 7,092,780 B2 | 8/2006 | Ganley et al. | |
| 7,234,938 B2 | 6/2007 | Bodenmiller | |
| 8,069,772 B1 * | 12/2011 | Peterson ............ | F15B 21/082 91/361 |
| 8,622,668 B2 | 1/2014 | Basler | |
| 8,721,237 B2 | 5/2014 | Basler | |
| 8,738,860 B1 * | 5/2014 | Griffin ............ | G06F 12/0897 711/122 |
| 2002/0034571 A1 * | 3/2002 | Zimmerman ............ | A21C 1/006 426/549 |

(Continued)

*Primary Examiner* — Tejal Gami
(74) *Attorney, Agent, or Firm* — Charles Fowler

(57) ABSTRACT

Apparatus for producing finished dental restorations at the dentist's chair side from 3D CAD data. These restorations may be manufactured from ceramics, metals and polymers via subtractive means i.e. milling and grinding. A polar compact mechanism has been employed with the implementation of an inverse kinematic transform in the machine control to allow Cartesian programming. The margin following tool path is very computationally intensive and requires many minutes of calculation time and numerical control programs in excess of 10 mb for a typical restoration. Conventionally this would require the user to wait several minutes before running the machine which would increase the wait time for both the patient and the doctor. This problem is solved by allowing the program to be generated in parallel with the machine in the process of actually cutting the restoration.

11 Claims, 7 Drawing Sheets

(56) References Cited

U.S. PATENT DOCUMENTS

| | | | |
|---|---|---|---|
| 2002/0196080 A1* | 12/2002 | Saito | H03F 3/45103 330/254 |
| 2004/0115015 A1 | 6/2004 | Sjostedt et al. | |
| 2004/0166462 A1 | 8/2004 | Phan et al. | |
| 2004/0187654 A1* | 9/2004 | Kato | B23Q 1/5412 82/1.11 |
| 2005/0261795 A1 | 11/2005 | Ghosh et al. | |
| 2006/0003292 A1 | 1/2006 | Lauren et al. | |
| 2006/0035776 A1* | 2/2006 | Duncan | B23B 31/103 483/30 |
| 2006/0091734 A1* | 5/2006 | Everman | F16L 3/00 310/12.06 |
| 2007/0243503 A1 | 10/2007 | Gagnon et al. | |
| 2008/0091295 A1* | 4/2008 | Corey | G05B 19/40937 700/178 |
| 2008/0095625 A1* | 4/2008 | Honegger | F03D 9/00 416/146 R |
| 2008/0164834 A1* | 7/2008 | Iwashita | G05B 19/404 318/571 |
| 2009/0053004 A1* | 2/2009 | Yamaura | B23Q 1/623 409/165 |
| 2009/0108497 A1* | 4/2009 | Chaslin | B29C 45/2725 264/297.3 |
| 2011/0044778 A1* | 2/2011 | Yamada | G05B 19/416 409/80 |
| 2011/0218780 A1* | 9/2011 | Yang | G06F 17/10 703/2 |
| 2012/0008952 A1* | 1/2012 | Li | H04B 10/50 398/65 |
| 2012/0029387 A1* | 2/2012 | Wei | A61B 90/36 600/587 |
| 2013/0006267 A1* | 1/2013 | Odermatt | B25J 9/1628 606/130 |
| 2013/0056892 A1* | 3/2013 | Johnson | A61C 13/0004 264/19 |
| 2013/0226534 A1* | 8/2013 | Fisker | G06F 17/50 703/1 |

* cited by examiner

CHAIR SIDE MILL FOR FABRICATING DENTAL RESTORATIONS

BACKGROUND OF THE INVENTION

Field of the Invention

The present invention pertains to apparatus for producing finished dental restorations at the dentist's chair side from 3D CAD data. These restorations include but are not limited to, crowns, bridges, abutments, veneers and surgical guides. These may be manufactured from ceramics, metals and polymers via subtractive means i.e. milling and grinding. This new system will deliver many advantages over currently available chair side systems including; reduced margin chipping, increased accuracy, improved reliability and reduced complexity in a smaller package.

Background Art

The polar configuration of one prior art chair side system creates a compact mechanism suitable for chair side usage but represents a compromise from a programming stand point since the system must be programmed using polar coordinates. Toolpath generation algorithms are not well adapted to this purpose and polar movements are restrictive in terms of the machining strategy that can be employed. Another prior art chair side machine has a Cartesian mechanism which allows simple flexible toolpath programming but results in a much larger and heavier mechanism that is at odds with the intended chair side environment.

Both of these prior art systems utilize a toolpath that employs a lacing motion which crosses the margin with each pass. This places an extremely high acceleration demand on the machine which results in corner rounding and also a discontinuity in cutting force, both of which compromise the integrity of the margin.

By contrast, the present invention utilizes a predominantly helical motion that traces the actual form of the margin line. This significantly reduces the acceleration demands of the programmed path and maintains a constant grinding pressure. This results in a dramatic improvement in the marginal fit and integrity of the finished crown. This type of motion is not well suited to the aforementioned prior art machines. When using two tools simultaneously, it would be very difficult to avoid collisions and the necessary avoidance moves would cause rapid discontinuities in the machine's motion that are themselves likely to lead to damage if occurring close to the crown's margin.

SUMMARY OF THE INVENTION

With this invention a polar mechanism has been employed to allow a compact mechanism with the implementation of an inverse kinematic transform in the machine control to allow Cartesian programming. Thus, maximum programming flexibility is maintained. This kind of control approach is commonly used with resolute joint and hexapod robots.

This margin following tool path is very computationally intensive and requires many minutes of calculation time and numerical control programs in excess of 10 mb for a typical restoration. Conventionally this would require the user to wait several minutes before running the machine which would increase the wait time for both the patient and the doctor. Even with the smaller programs, this wait time has been observed to be a hindrance for the user.

The present invention solves this problem by allowing the program to be generated in parallel with the machine in the process of actually cutting the restoration. The program geometry is divided into small sections or sub-programs and passed to the machine as each section becomes ready. In this method a main program telling the machine what type of material and restoration is to be manufactured, is sent to the machine instantaneously allowing the user to load the material and start the process. This program also tells the machine how many subsequent programs it should expect to receive, the first of which takes only a few seconds to generate. The machine begins cutting material at once. By the time the machine has finished with the first sub-program, the second one is ready and so on.

The mechanism of the machine employs toothed belt driven rotary axes that enable high acceleration and low hysteresis when compared to other cost appropriate rotary axis designs such as split gear drive or a conventional worm gear. A single linear axis in the machine utilizes a static ball screw with rotating nut and open frame servo motor built around the nut. This design significantly reduces the rotating inertia over a conventional static nut and rotating screw design and so facilitates extremely high acceleration rates. The resulting mechanism is capable of up to 3 G acceleration on all axes. Conventional machine tools typically have only a 0.5-1 G acceleration capability by contrast. In accordance with micro machining principles, this high acceleration allows high feed rates to be maintained while following contours that are continually changing direction, with minimal deviation from the programmed path. This makes cycle times of approximately 10-18 minutes possible even with a single tool in cut at any one time.

High acceleration capability alone is not enough to achieve high feed rates without sacrificing machining conditions and output quality. The aforementioned prior art machines utilize 40-60,000 rpm direct driven electric spindles which limit the magnitude of the feed rates possible. Achieving higher rotary speeds with electric motors adds significant cost and size not appropriate to the restoration chair side application. Therefore, in the preferred embodiment a 150,000 rpm air turbine spindle is used which has less than 1 micron Total Indicated Run-out (TIR) and low heating. As a result, the machine can maintain good machining conditions up to 4 m/min as opposed to less than 2 m/min for prior art chair side machines.

BRIEF DESCRIPTION OF THE DRAWINGS

The aforementioned objects and advantages of the present invention, as well as additional objects and advantages thereof, will be more fully understood herein after as a result of a detailed description of a preferred embodiment when taken in conjunction with the following drawings in which.

DETAILED DESCRIPTION OF A PREFERRED EMBODIMENT

The preferred embodiment of the invention consists of a CAM system that may be or may not be on an external PC. This CAM system takes a standard CAD input of a dental restoration such as stl or iges and creates manufacturing instructions which are sent wirelessly in sections to a tablet PC which forms the human-to-machine interface or HMI for the machine. The HMI communicates with a CNC controller that converts these instructions to real time motion commands. These commands move multiple axes creating relative motion between a spindle and blank piece of material which allows the piece to be cut into a finished dental restoration.

CAM

Any general CAM software can be adapted to this application; a unique feature is the use of helical motion concentric to the margin line and the passing of small sections of code in sequence that the machine can execute while subsequent instructions are calculated by the CAM computer. These instructions are generated in a Cartesian coordinate system.

Control System

Figure 2:
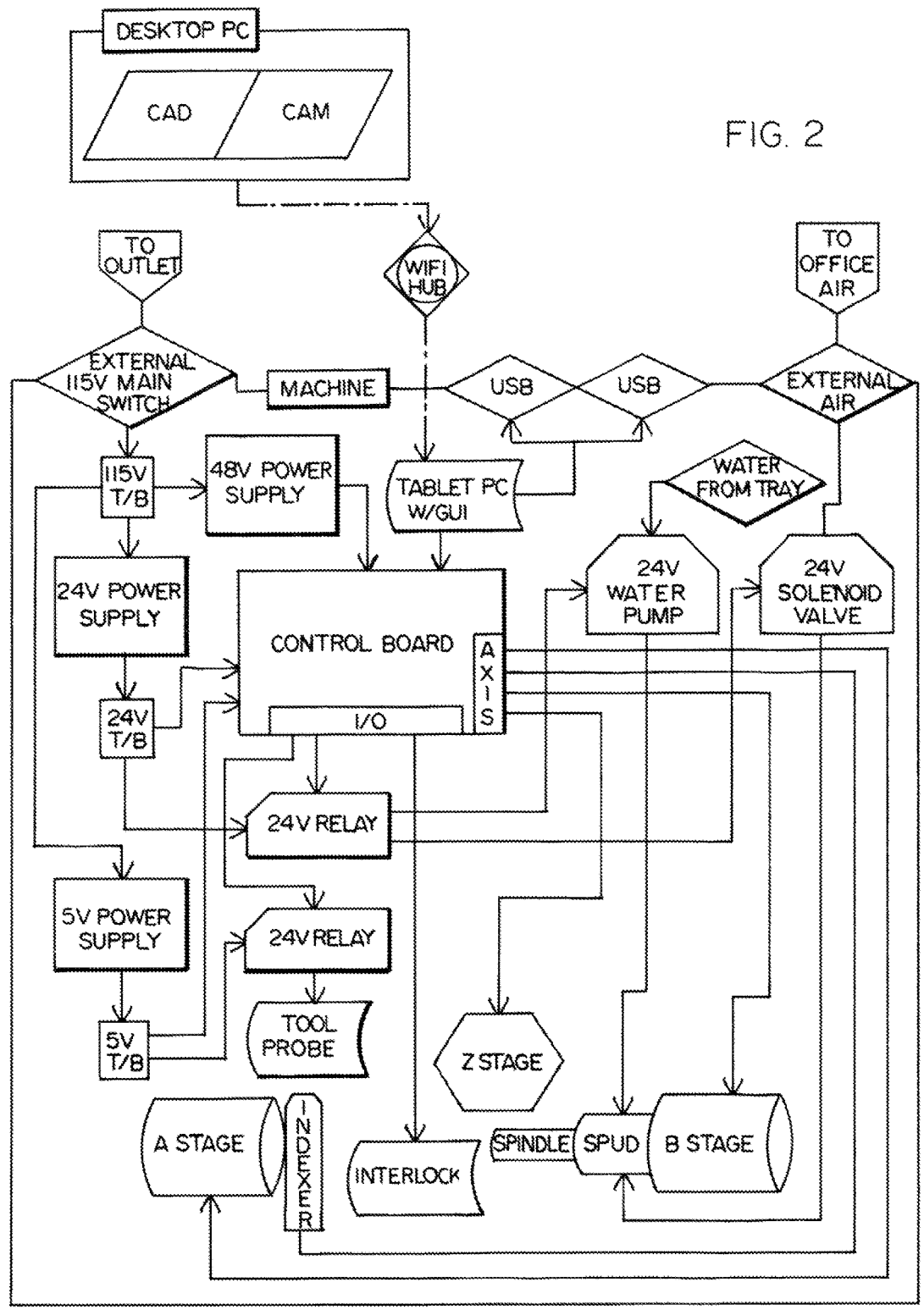
FIG. 2 is a schematic of the machine of FIG. 1.

Details of the control system and its relationship to the mechanical systems can be seen in FIG. 2. The GUI/HMI allows the user to interact with the machine to load programs, move the machine to access positions for loading tools and material, track tool life and diagnostic functionality for technician level operators. The GUI/HMI receives manufacturing instructions in terms of Cartesian positions and ideal speeds of motion. These parameters are converted via a kinematic transform to polar and linear commands for the corresponding axes. As this trajectory planning is performed and buffered, the real time control sends commands to the individual axes. This may be open loop or closed loop and the position loop may be closed at the drive level or the control level. The control also handles the starting and stopping, air and water and other ancillary tasks.

Mechanism

A simple rigid box structure supports the basic motion control mechanism which consists of a statically mounted linear Z axis mounted directly to the structure, a dynamically mounted rotary B axis that is carried by the linear stage and an opposing statically mounted A axis rotary that is offset 40 mm with respect to the center of the B rotary axis. These axis relationships can be seen in FIGS. 1 and 4.

The linear axis could take any form of conventional ball screw, belt drive, rack and pinion, friction drive, direct driven linear motor, etc. It may be driven via a servo motor or open or closed loop stepper motor. It's important qualities are high rigidity, high acceleration, low backlash and proportionately high resolution. The rotary axes may be belt driven, driven by friction drive or by direct drive. It is important that the rotary axis provides high rigidity, high acceleration, low backlash and proportionately high resolution. Worm and worm gear, planetary gears and harmonic drives are deemed unsuitable due to high friction, backlash or inertia. The selected mechanism should provide a continuous acceleration capability of more than 2 G which is far in excess of any similar dental machines and the sole domain of highly sophisticated industrial machinery for high speed and micro machining. The axes may reference themselves to a home position via the use of an auxiliary sensor placed at a point in the travel or by the use of hard stop. Hard stop homing is only possible with a closed loop system as it necessary to sense the position of the hard stop via an increase in following error.

A spindle is also carried on the dynamically mounted rotary axis at a radius of 30 mm. The spindle can be translated axially with respect to the spindle rotation by the movement of the linear Z axis. Important qualities of this spindle are high RPM to achieve surface speeds up to 6500 SFM, (optimal for grinding of ceramics), low Total Indicated Run-out (TIR) to keep a consistent load on the grinding or milling tool, low mass to reduce inertial loading on the motion system and low heat generation to prevent thermal growth and a subsequent reduction in accuracy. These qualities are exhibited by high precision air turbine spindles that are conventionally used in high speed milling operations and jig grinding, but not in dental specific machinery. This spindle also lends itself well to adaptive control via acoustic emission monitoring, since load is highly audible. It is possible to use other spindle technology with similar qualities.

The statically mounted B axis rotary carries another rotary axis termed an "indexer". The indexer supports the material to be machined at a radius of 30 mm. The indexer allows access to the work piece from multiple angles and it may be electrically or pneumatically driven, open or closed loop and used for non-simultaneous positioning or full simultaneous motion with the other axes. It may also support a piezo electric actuator or other means ultrasonically exciting the work piece.

Figure 4:
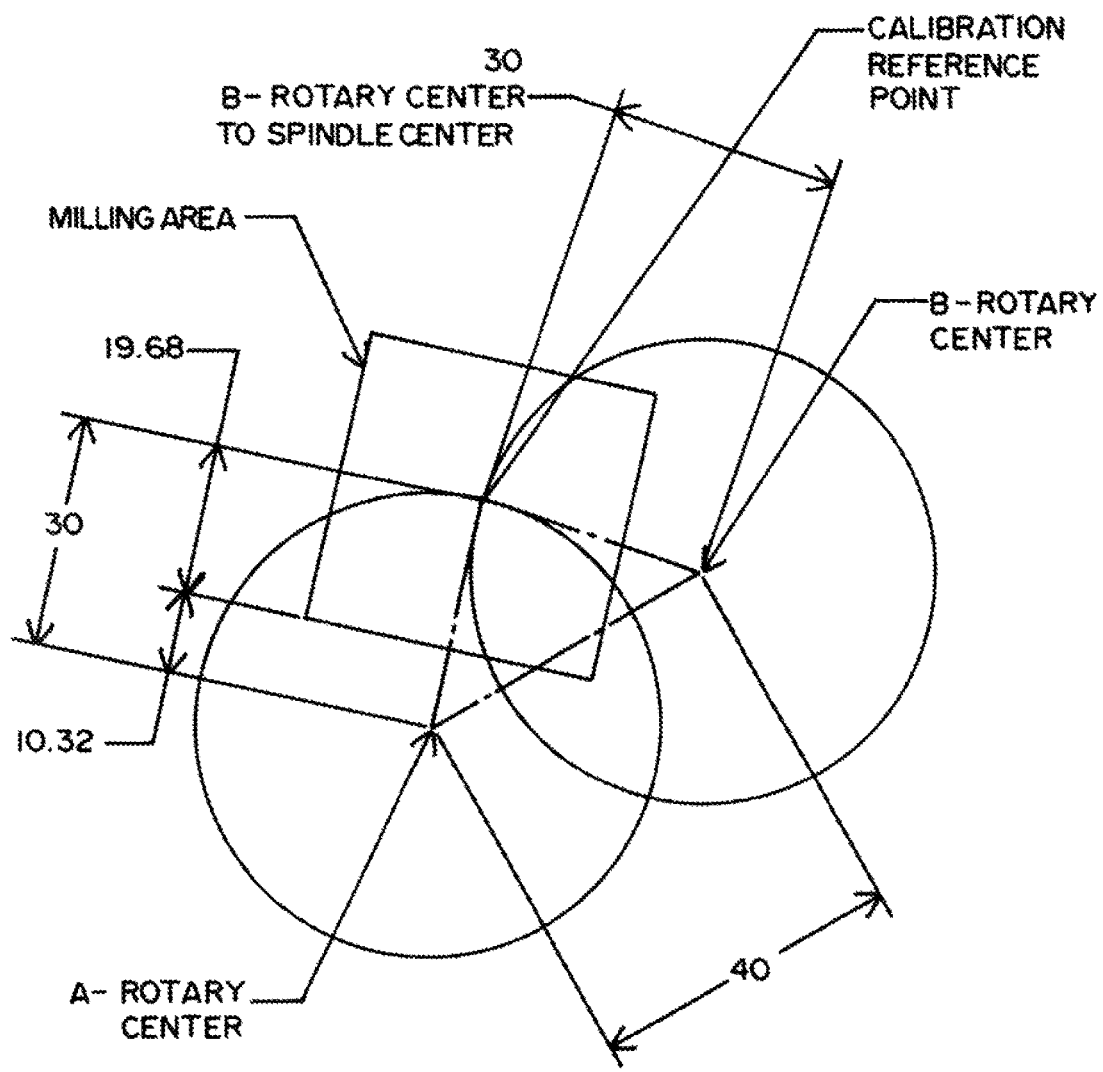
FIG. 4 is geometric representation of the polar and Cartesian travel envelope of the cutting tool of the preferred embodiment.
Figure 5:
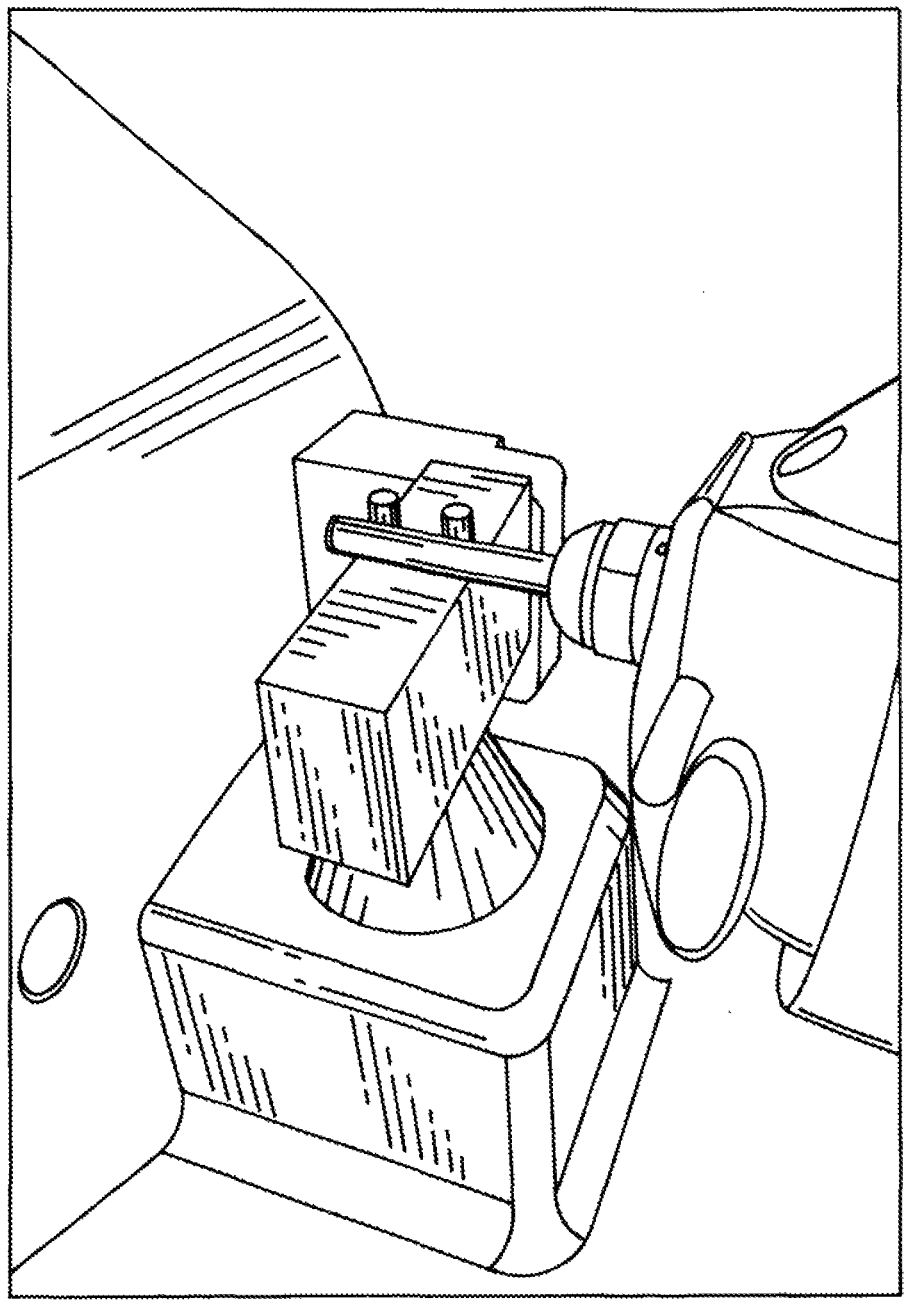
FIG. 5 is an illustration of the referencing of the rotary axes of the preferred embodiment.
Figure 6:
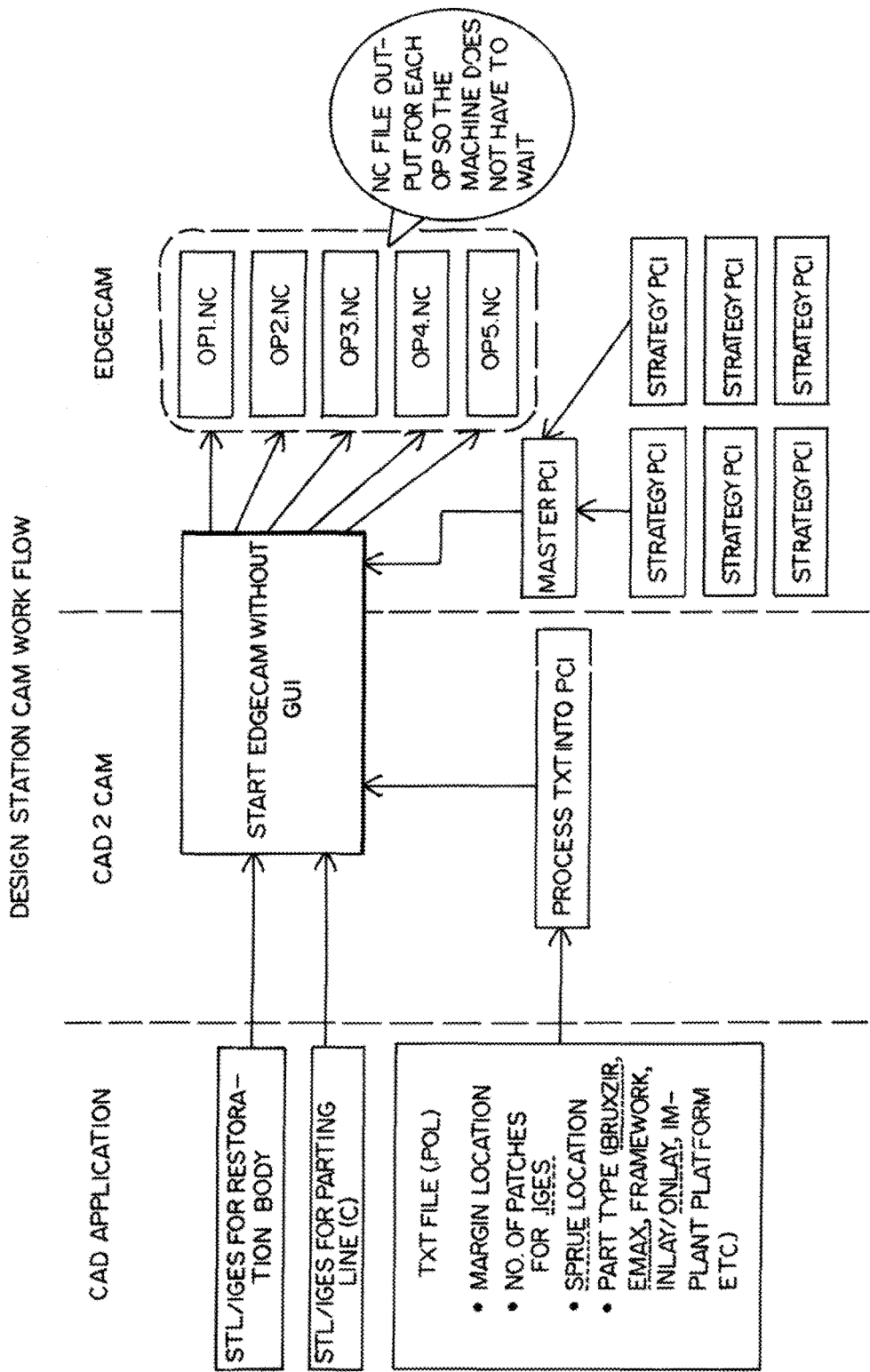
FIG. 6 is a flow chart of the data flow between CAD and CAM to the machine of FIG. 1.
Figure 7:
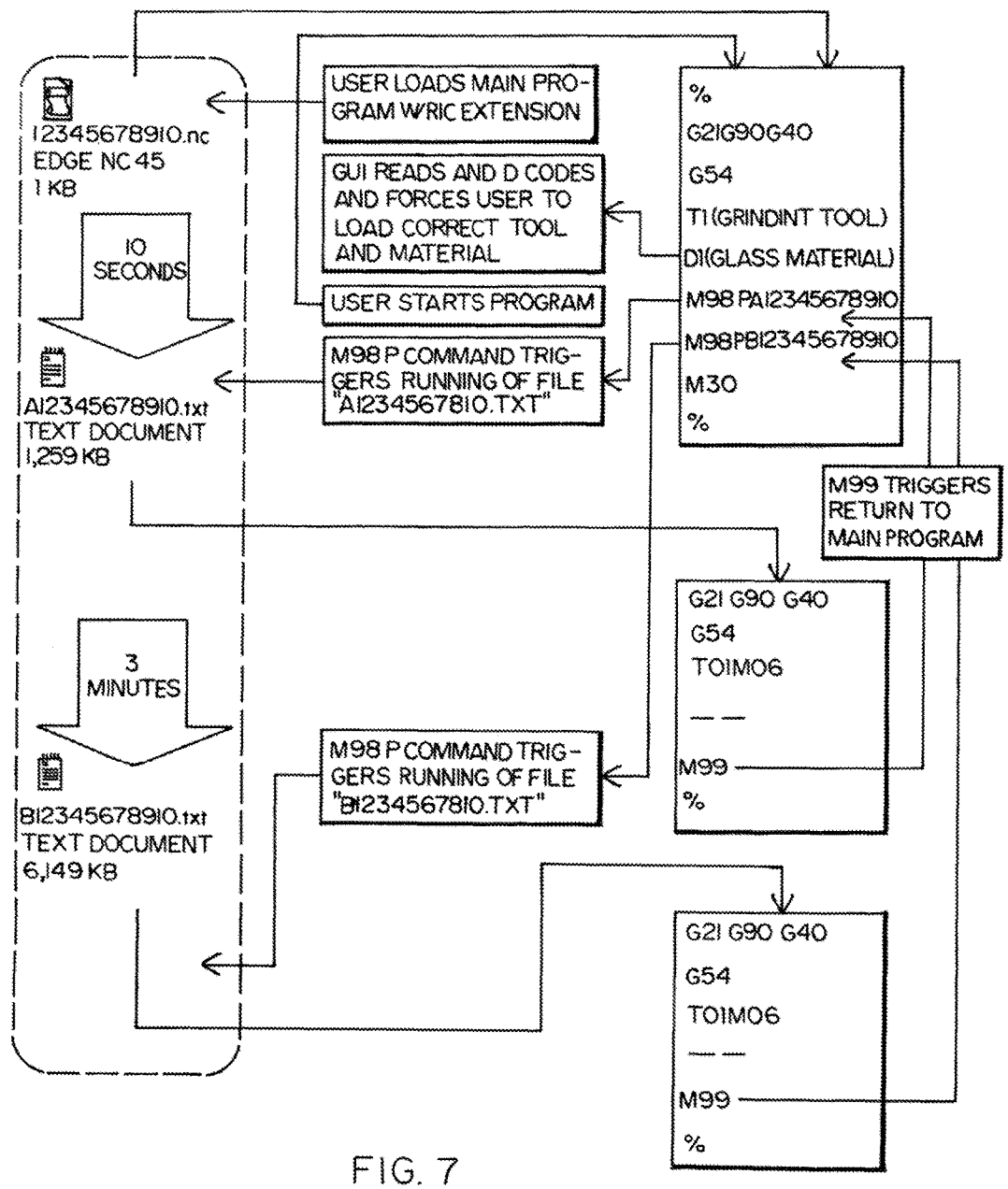
FIG. 7 is a flow chart drawing of the simultaneous generation and execution of numerical control files in the preferred embodiment.

In FIG. 4 it can be seen that the intersection of the two rotary axes provides an equivalent Cartesian travel envelope sufficient for manufacturing many dental restorations up to and including small bridges. In order to reference the rotary axes with respect to one another, a pin gauge of precision dimensions is placed in the spindle and a tooling block that allows the pin in the spindle to be positioned at a 30 mm radius with respect to the A rotary, is held on the indexer material holder. This operation can be seen in FIG. 5. Once this has been performed, the control then records this neutral position as described in FIG. 4 relative to the home position of each axis.

The preferred embodiment also includes means of measuring the position of the tool tip in the z axis to take account of the variance of placement of the tool in the spindle. This may be by means of a high precision switch, an optical sensor or by monitoring "following error" when driven against a reference surface (similar to hard stop homing).

Figure 1:
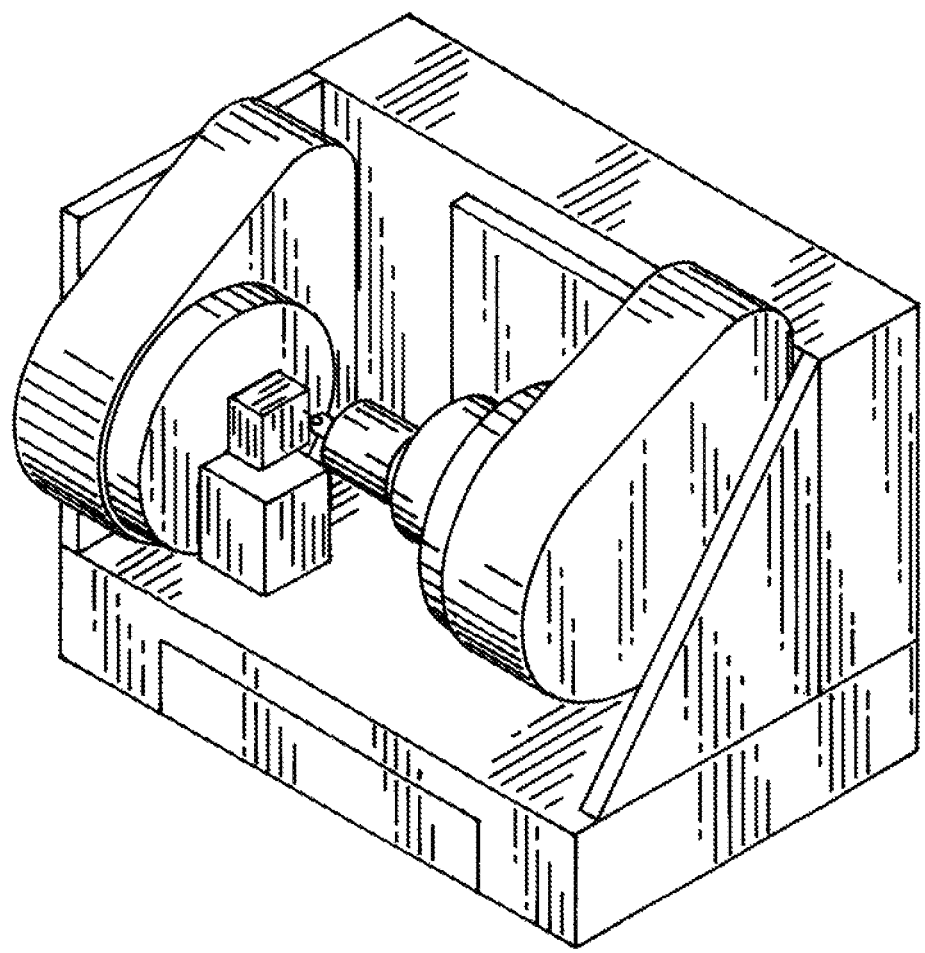
FIG. 1 is a machine level representation of a preferred embodiment of a chair side dental restoration fabrication machine of the present invention.
Figure 3:
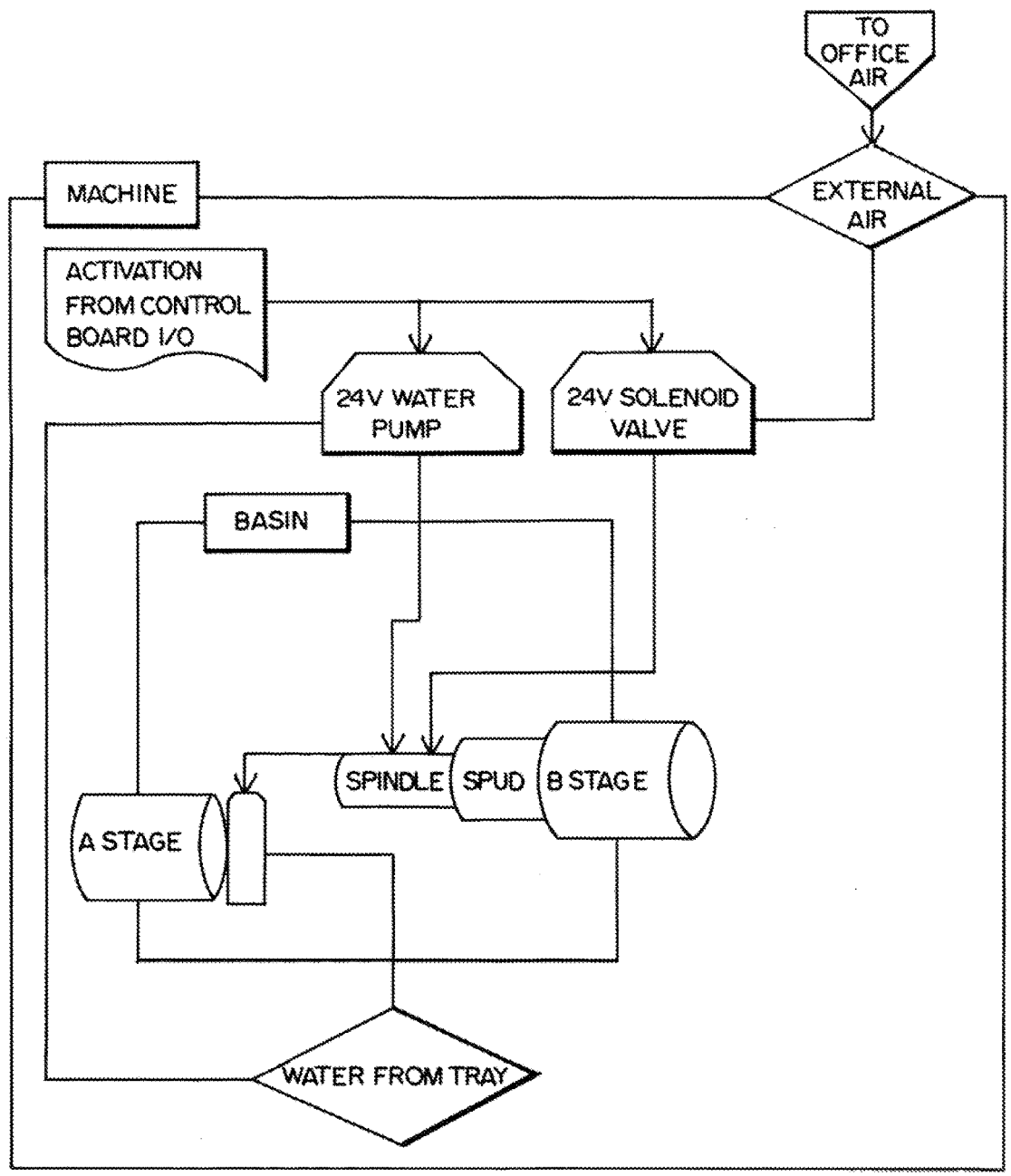
FIG. 3 is a coolant/air system schematic of the preferred embodiment.

FIGS. 1 and 3 show a simple coolant supply system that is used to provide cooling, lubrication and material removal for the machining process.

The present invention is thus seen to be uniquely capable of dental restoration milling in a small chair side setting wherein a finished component is fabricated in a relatively short period of time. A polar mechanism with Cartesian programming relies on parallel processing to achieve highly complex and accurate material removal in a precise surface geometry. While a preferred embodiment has been disclosed herein, it will be understood that various modifications and additions are contemplated without deviating from the inventive features hereof. Accordingly, the scope hereof is to be limited only by the appended claims and their equivalents.

We claim:

1. A dental restoration milling apparatus for producing a restoration from a workpiece, the apparatus comprising:

a computer program-controlled rotating spindle with an attached tool for removing material from the workpiece to produce the restoration;

a multi-axis rotary tool control system positioning the computer program-controlled rotating spindle with an attached tool on a path, the multi-axis rotary tool control system comprising at least two rotary axis controls that control at least a pair of opposed rotary axes, wherein at least one of the pair of opposed rotary axes is rotated to position the rotating spindle with an attached tool, wherein the at least one opposed rotary axis is distinct from the rotating spindle with an attached tool and has an axis of rotation that is parallel with an axis of rotation of the rotating spindle with an attached tool, and wherein the pair of opposed rotary axes has an offset between each other;

a computer and a tool positioning program controlling the computer to instruct the multi-axis rotary tool control system where and to what extent for the tool attached to the rotating spindle to remove the material from the workpiece.

2. The dental restoration milling apparatus recited in claim 1 wherein the computer and the tool positioning program are configured to receive instructions for tool positioning in accordance with a Cartesian coordinate system and carry out actual tool positioning in a polar and linear coordinate system.

3. The dental restoration milling apparatus recited in claim 1 wherein the tool positioning program comprises a plurality of sequential subprograms and the computer is configured to generate the plurality of sequential subprograms and sequentially instruct the multi-axis rotary tool control system to position the rotating spindle with an attached tool according to each of the subprograms even as others of the subprograms are being generated by the computer.

4. The dental restoration milling apparatus recited in claim 1 wherein the multi-axis rotary tool control system comprises a linear axis control.

5. The dental restoration milling apparatus recited in claim 1 wherein rotary axis controls are capable of accelerating the multi-axis rotary tool greater than 2 G's.

6. The dental restoration milling apparatus recited in claim 1 wherein the workpiece is mounted on an indexer rotary axis of the pair of the opposed rotary axes for altering the rotary position of the workpiece.

7. The dental restoration milling apparatus recited in claim 1 further comprising a tool tip position sensor for determining the instantaneous position of the tool relative to the workpiece.

8. The dental restoration milling apparatus recited in claim 1 wherein at least one of the opposed rotary axes of the multi-axis rotary tool control system comprises an air turbine spindle.

9. The dental restoration milling apparatus recited in claim 8 wherein said air turbine spindle is rotated at up to 150,000 RPM and has less than a 1 micron TIR.

10. The dental restoration milling apparatus recited in claim 1 wherein one of the pair of opposed rotary axes controls a rotary position of the rotating spindle with an attached tool and one of the pair of opposed rotary axes controls a rotary position of the workpiece.

11. The dental restoration milling apparatus recited in claim 1 wherein the multi-axis rotary tool control system tracks the position of the rotating spindle with an attached tool relative to the workpiece as the material is removed.

* * * * *